(12) United States Patent
Sambelashvili et al.

(10) Patent No.: US 9,289,612 B1
(45) Date of Patent: Mar. 22, 2016

(54) COORDINATION OF VENTRICULAR PACING IN A LEADLESS PACING SYSTEM

(71) Applicant: Medtronic, Inc., Minneapolis, MN (US)

(72) Inventors: Aleksandre T Sambelashvili, Maple Grove, MN (US); Yong K Cho, Excelsior, MN (US); Todd J Sheldon, North Oaks, MN (US)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 14/567,609

(22) Filed: Dec. 11, 2014

(51) Int. Cl.
*A61N 1/00* (2006.01)
*A61N 1/368* (2006.01)
*A61N 1/375* (2006.01)

(52) U.S. Cl.
CPC .............. *A61N 1/3682* (2013.01); *A61N 1/368* (2013.01); *A61N 1/3756* (2013.01)

(58) Field of Classification Search
CPC . A61N 1/37288; A61N 1/37211; A61N 1/362
USPC .................................. 607/32, 59, 60
See application file for complete search history.

(56) References Cited

U.S. PATENT DOCUMENTS

| 3,486,506 | A | 12/1969 | Auphan |
|---|---|---|---|
| 3,659,615 | A | 5/1972 | Enger |
| 3,693,625 | A | 9/1972 | Auphan |
| 3,835,864 | A | 9/1974 | Rasor et al. |
| 3,943,936 | A | 3/1976 | Rasor et al. |
| 4,157,720 | A | 6/1979 | Greatbatch |
| RE30,366 | E | 8/1980 | Rasor et al. |
| 4,256,115 | A | 3/1981 | Bilitch |
| 4,333,469 | A | 6/1982 | Jeffcoat et al. |
| 5,170,784 | A | 12/1992 | Ramon et al. |
| 5,193,539 | A | 3/1993 | Schulman et al. |
| 5,193,540 | A | 3/1993 | Schulman et al. |

(Continued)

FOREIGN PATENT DOCUMENTS

| CN | 101185789 A | 5/2008 |
|---|---|---|
| CN | 101284160 A | 10/2008 |

(Continued)

OTHER PUBLICATIONS

Delnoy, Peter Paul et al., "Validation of a peak endocardial acceleration-based algorithm to optimize cardiac resynchronization: early clinical results," *Europace*, 10:801-8 (2008).

(Continued)

*Primary Examiner* — Amanda Patton
*Assistant Examiner* — Philip Edwards
(74) *Attorney, Agent, or Firm* — Evans M Mburu

(57) ABSTRACT

An implantable medical system is configured to coordinate ventricular pacing with intrinsic depolarizations of another chamber. The implantable medical system includes a leadless pacing device implanted on or within the ventricle. Another implantable medical device is configured to sense an intrinsic depolarization the other chamber of the heart of the patient, and in response to the intrinsic depolarization of the other chamber, deliver an electrical pulse. The leadless pacing device is configured to detect the electrical pulse delivered by the other implantable medical device and, in response to detecting the electrical pulse delivered by the other implantable medical device, deliver a pacing pulse to the ventricle via at least a first electrode in coordination with the intrinsic depolarization of the other chamber.

21 Claims, 8 Drawing Sheets

(56) References Cited

U.S. PATENT DOCUMENTS

| | | |
|---|---|---|
| 5,243,977 A | 9/1993 | Trabucco et al. |
| 5,312,439 A | 5/1994 | Loeb |
| 5,324,316 A | 6/1994 | Schulman et al. |
| 5,404,877 A | 4/1995 | Nolan et al. |
| 5,405,367 A | 4/1995 | Schulman et al. |
| 5,411,535 A | 5/1995 | Fujii et al. |
| 5,441,527 A | 8/1995 | Erickson et al. |
| 5,674,259 A | 10/1997 | Gray |
| 5,792,208 A | 8/1998 | Gray |
| 5,814,089 A | 9/1998 | Stokes et al. |
| 5,843,132 A | 12/1998 | Ilvento |
| 5,895,414 A | 4/1999 | Sanchez-Zambrano |
| 5,954,757 A | 9/1999 | Gray |
| 5,970,986 A | 10/1999 | Bolz et al. |
| 5,987,352 A | 11/1999 | Klein et al. |
| 6,044,300 A | 3/2000 | Gray |
| 6,051,017 A | 4/2000 | Loeb et al. |
| 6,141,588 A | 10/2000 | Cox et al. |
| 6,144,879 A | 11/2000 | Gray et al. |
| 6,175,764 B1 | 1/2001 | Loeb et al. |
| 6,181,965 B1 | 1/2001 | Loeb et al. |
| 6,185,452 B1 | 2/2001 | Schulman et al. |
| 6,185,455 B1 | 2/2001 | Loeb et al. |
| 6,208,894 B1 | 3/2001 | Schulman et al. |
| 6,214,032 B1 | 4/2001 | Loeb et al. |
| 6,240,316 B1 | 5/2001 | Richmond et al. |
| 6,315,721 B2 | 11/2001 | Schulman et al. |
| 6,415,184 B1 | 7/2002 | Ishikawa et al. |
| 6,445,953 B1 | 9/2002 | Bulkes et al. |
| 6,592,518 B2 | 7/2003 | Denker et al. |
| 6,628,989 B1 | 9/2003 | Penner et al. |
| 6,654,638 B1 | 11/2003 | Sweeney |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,672 B2 | 5/2004 | Schulman et al. |
| 6,764,446 B2 | 7/2004 | Wolinsky et al. |
| 6,788,975 B1 | 9/2004 | Whitehurst et al. |
| 6,804,561 B2 | 10/2004 | Stover |
| 6,871,099 B1 | 3/2005 | Whitehurst et al. |
| 6,907,285 B2 | 6/2005 | Denker et al. |
| 6,917,833 B2 | 7/2005 | Denker et al. |
| 6,941,171 B2 | 9/2005 | Mann et al. |
| 6,947,782 B2 | 9/2005 | Schulman et al. |
| 7,003,350 B2 | 2/2006 | Denker et al. |
| 7,006,864 B2 | 2/2006 | Echt et al. |
| 7,024,248 B2 | 4/2006 | Penner et al. |
| 7,050,849 B2 | 5/2006 | Echt et al. |
| 7,054,692 B1 | 5/2006 | Whitehurst et al. |
| 7,082,336 B2 | 7/2006 | Ransbury et al. |
| 7,103,408 B2 | 9/2006 | Haller et al. |
| 7,114,502 B2 | 10/2006 | Schulman et al. |
| 7,120,992 B2 | 10/2006 | He et al. |
| 7,132,173 B2 | 11/2006 | Daulton |
| 7,167,751 B1 | 1/2007 | Whitehurst et al. |
| 7,177,698 B2 | 2/2007 | Klosterman et al. |
| 7,184,830 B2 | 2/2007 | Echt et al. |
| 7,198,603 B2 | 4/2007 | Penner et al. |
| 7,200,437 B1 | 4/2007 | Nabutovsky et al. |
| 7,203,548 B2 | 4/2007 | Whitehurst et al. |
| 7,214,189 B2 | 5/2007 | Zdeblick |
| 7,236,821 B2 | 6/2007 | Cates et al. |
| 7,236,829 B1 | 6/2007 | Farazi et al. |
| 7,260,436 B2 | 8/2007 | Kilgore et al. |
| 7,283,874 B2 | 10/2007 | Penner |
| 7,286,883 B2 | 10/2007 | Schulman et al. |
| 7,292,890 B2 | 11/2007 | Whitehurst et al. |
| 7,294,108 B2 | 11/2007 | Bornzin et al. |
| 7,295,879 B2 | 11/2007 | Denker et al. |
| 7,310,556 B2 | 12/2007 | Bulkes |
| 7,330,756 B2 | 2/2008 | Marnfeldt |
| 7,343,204 B2 | 3/2008 | Schulman et al. |
| 7,351,921 B1 | 4/2008 | Haller et al. |
| 7,363,082 B2 | 4/2008 | Ransbury et al. |
| 7,428,438 B2 | 9/2008 | Parramon et al. |
| 7,437,193 B2 | 10/2008 | Parramon et al. |
| 7,444,180 B2 | 10/2008 | Kuzma et al. |
| 7,450,998 B2 | 11/2008 | Zilberman et al. |
| 7,493,172 B2 | 2/2009 | Whitehurst et al. |
| 7,513,257 B2 | 4/2009 | Schulman et al. |
| 7,519,421 B2 | 4/2009 | Denker et al. |
| 7,519,424 B2 | 4/2009 | Dennis et al. |
| 7,529,589 B2 | 5/2009 | Williams et al. |
| 7,532,932 B2 | 5/2009 | Denker et al. |
| 7,532,933 B2 | 5/2009 | Hastings et al. |
| 7,535,296 B2 | 5/2009 | Bulkes et al. |
| 7,555,345 B2 | 6/2009 | Wahlstrand et al. |
| 7,558,631 B2 | 7/2009 | Cowan et al. |
| 7,565,195 B1 | 7/2009 | Kroll et al. |
| 7,587,241 B2 | 9/2009 | Parramon et al. |
| 7,606,621 B2 | 10/2009 | Brisken et al. |
| 7,610,092 B2 | 10/2009 | Cowan et al. |
| 7,616,990 B2 | 11/2009 | Chavan et al. |
| 7,616,992 B2 | 11/2009 | Dennis et al. |
| 7,617,007 B2 | 11/2009 | Williams et al. |
| 7,627,371 B2 | 12/2009 | Wang et al. |
| 7,627,376 B2 | 12/2009 | Dennis et al. |
| 7,627,383 B2 | 12/2009 | Haller et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,640,061 B2 | 12/2009 | He et al. |
| 7,647,109 B2 | 1/2010 | Hastings et al. |
| 7,650,186 B2 | 1/2010 | Hastings et al. |
| 7,706,892 B2 | 4/2010 | Colvin et al. |
| 7,713,194 B2 | 5/2010 | Zdeblick |
| 7,734,343 B2 | 6/2010 | Ransbury et al. |
| 7,747,335 B2 | 6/2010 | Williams |
| 7,751,881 B2 | 7/2010 | Cowan et al. |
| 7,766,216 B2 | 8/2010 | Daulton |
| 7,771,838 B1 | 8/2010 | He et al. |
| 7,781,683 B2 | 8/2010 | Haller et al. |
| 7,809,438 B2 | 10/2010 | Echt et al. |
| 7,822,480 B2 | 10/2010 | Park et al. |
| 7,826,903 B2 | 11/2010 | Denker et al. |
| 7,840,282 B2 | 11/2010 | Williams et al. |
| 7,848,815 B2 | 12/2010 | Brisken et al. |
| 7,848,823 B2 | 12/2010 | Drasler et al. |
| 7,860,564 B2 | 12/2010 | Root et al. |
| 7,860,570 B2 | 12/2010 | Whitehurst et al. |
| 7,890,173 B2 | 2/2011 | Brisken et al. |
| 7,894,907 B2 | 2/2011 | Cowan et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,904,167 B2 | 3/2011 | Klosterman et al. |
| 7,930,031 B2 | 4/2011 | Penner |
| 7,937,148 B2 | 5/2011 | Jacobson |
| 7,945,333 B2 | 5/2011 | Jacobson |
| 7,957,805 B2 | 6/2011 | He |
| 7,979,126 B2 | 7/2011 | Payne et al. |
| 7,991,467 B2 | 8/2011 | Markowitz et al. |
| 7,996,097 B2 | 8/2011 | DiBernardo et al. |
| 8,010,209 B2 | 8/2011 | Jacobson |
| 8,019,419 B1 | 9/2011 | Panescu et al. |
| 8,032,219 B2 | 10/2011 | Neumann et al. |
| 8,032,227 B2 | 10/2011 | Parramon et al. |
| 8,078,279 B2 | 12/2011 | Dennis et al. |
| 8,078,283 B2 | 12/2011 | Cowan et al. |
| 8,116,883 B2 | 2/2012 | Williams et al. |
| 8,126,561 B2 | 2/2012 | Chavan et al. |
| 8,127,424 B2 | 3/2012 | Haller et al. |
| 8,165,696 B2 | 4/2012 | McClure et al. |
| 8,185,212 B2 | 5/2012 | Carbunaru et al. |
| 8,204,595 B2 | 6/2012 | Pianca et al. |
| 8,224,449 B2 | 7/2012 | Carbunaru et al. |
| 8,239,045 B2 | 8/2012 | Ransbury et al. |
| 8,295,939 B2 | 10/2012 | Jacobson |
| 8,301,242 B2 | 10/2012 | Root et al. |
| 8,301,262 B2 | 10/2012 | Mi et al. |
| 8,311,627 B2 | 11/2012 | Root et al. |
| 8,315,701 B2 | 11/2012 | Cowan et al. |
| 8,321,036 B2 | 11/2012 | Brockway et al. |

(56) References Cited

U.S. PATENT DOCUMENTS

| | | |
|---|---|---|
| 8,332,036 B2 | 12/2012 | Hastings et al. |
| 8,340,780 B2 | 12/2012 | Hastings et al. |
| 8,352,025 B2 | 1/2013 | Jacobson |
| 8,352,028 B2 | 1/2013 | Wenger |
| 8,359,098 B2 | 1/2013 | Lund et al. |
| 8,364,267 B2 | 1/2013 | Schleicher et al. |
| 8,364,276 B2 | 1/2013 | Willis |
| 8,364,278 B2 | 1/2013 | Pianca et al. |
| 8,364,280 B2 | 1/2013 | Marnfeldt et al. |
| 8,368,051 B2 | 2/2013 | Ting et al. |
| 8,374,696 B2 | 2/2013 | Sanchez et al. |
| 8,457,742 B2 | 6/2013 | Jacobson |
| 8,478,408 B2 | 7/2013 | Hastings et al. |
| 8,478,431 B2 | 7/2013 | Griswold et al. |
| 8,489,205 B2 | 7/2013 | Stotts et al. |
| 8,494,637 B2 | 7/2013 | Cowan et al. |
| 8,494,642 B2 | 7/2013 | Cowan et al. |
| 8,494,644 B2 | 7/2013 | Cowan et al. |
| 8,504,156 B2 | 8/2013 | Bonner et al. |
| 8,527,068 B2 | 9/2013 | Ostroff |
| 8,532,790 B2 | 9/2013 | Griswold |
| 8,541,131 B2 | 9/2013 | Lund et al. |
| 8,543,190 B2 | 9/2013 | Wasson et al. |
| 8,543,204 B2 | 9/2013 | Demmer et al. |
| 8,543,205 B2 | 9/2013 | Ostroff |
| 8,543,216 B2 | 9/2013 | Carbunaru et al. |
| 8,548,605 B2 | 10/2013 | Ollivier |
| 8,560,892 B2 | 10/2013 | Nicholes |
| 8,565,897 B2 | 10/2013 | Regnier et al. |
| 8,588,926 B2 | 11/2013 | Moore et al. |
| 8,626,294 B2 | 1/2014 | Sheldon et al. |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,922 B2 | 2/2014 | Root et al. |
| 8,660,660 B2 | 2/2014 | Dai et al. |
| 8,670,842 B1 | 3/2014 | Bornzin et al. |
| 2003/0114905 A1 | 6/2003 | Kuzma |
| 2004/0015204 A1 | 1/2004 | Whitehurst et al. |
| 2004/0073267 A1 | 4/2004 | Holzer |
| 2004/0093039 A1 | 5/2004 | Schumert |
| 2004/0122477 A1 | 6/2004 | Whitehurst et al. |
| 2004/0133242 A1 | 7/2004 | Chapman et al. |
| 2004/0147973 A1 | 7/2004 | Hauser |
| 2004/0162590 A1 | 8/2004 | Whitehurst et al. |
| 2004/0172089 A1 | 9/2004 | Whitehurst et al. |
| 2005/0055061 A1 | 3/2005 | Holzer |
| 2005/0070962 A1 | 3/2005 | Echt et al. |
| 2005/0256549 A1 | 11/2005 | Holzer |
| 2005/0288717 A1 | 12/2005 | Sunagawa |
| 2006/0074449 A1 | 4/2006 | Denker et al. |
| 2006/0135999 A1 | 6/2006 | Bodner et al. |
| 2006/0136005 A1 | 6/2006 | Brisken et al. |
| 2006/0173497 A1 | 8/2006 | Mech et al. |
| 2006/0241705 A1 | 10/2006 | Neumann et al. |
| 2006/0241732 A1 | 10/2006 | Denker et al. |
| 2007/0027508 A1 | 2/2007 | Cowan et al. |
| 2007/0060961 A1 | 3/2007 | Echt et al. |
| 2007/0073353 A1 | 3/2007 | Rooney et al. |
| 2007/0075905 A1 | 4/2007 | Denker et al. |
| 2007/0078490 A1 | 4/2007 | Cowan et al. |
| 2007/0088396 A1 | 4/2007 | Jacobson |
| 2007/0088397 A1 | 4/2007 | Jacobson |
| 2007/0106332 A1 | 5/2007 | Denker et al. |
| 2007/0106357 A1 | 5/2007 | Denker et al. |
| 2007/0118187 A1 | 5/2007 | Denker et al. |
| 2007/0129773 A1 | 6/2007 | Bulkes |
| 2007/0135883 A1 | 6/2007 | Drasler et al. |
| 2007/0150037 A1 | 6/2007 | Hastings et al. |
| 2007/0156204 A1 | 7/2007 | Denker et al. |
| 2007/0185538 A1 | 8/2007 | Denker et al. |
| 2007/0210862 A1 | 9/2007 | Denker et al. |
| 2007/0219590 A1 | 9/2007 | Hastings et al. |
| 2007/0276444 A1 | 11/2007 | Gelbart et al. |
| 2007/0288076 A1 | 12/2007 | Bulkes et al. |
| 2007/0288077 A1 | 12/2007 | Bulkes et al. |
| 2007/0293904 A1 | 12/2007 | Gelbart et al. |
| 2007/0293908 A1 | 12/2007 | Cowan et al. |
| 2007/0293912 A1 | 12/2007 | Cowan et al. |
| 2007/0293913 A1 | 12/2007 | Cowan et al. |
| 2008/0033497 A1 | 2/2008 | Bulkes et al. |
| 2008/0039904 A1 | 2/2008 | Bulkes et al. |
| 2008/0051854 A1 | 2/2008 | Bulkes et al. |
| 2008/0058886 A1 | 3/2008 | Williams |
| 2008/0077184 A1 | 3/2008 | Denker et al. |
| 2008/0077188 A1 | 3/2008 | Denker et al. |
| 2008/0097529 A1 | 4/2008 | Parramon et al. |
| 2008/0109054 A1 | 5/2008 | Hastings et al. |
| 2008/0119911 A1 | 5/2008 | Rosero |
| 2008/0132961 A1 | 6/2008 | Jaax et al. |
| 2008/0140154 A1 | 6/2008 | Loeb et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0319502 A1 | 12/2008 | Sunagawa et al. |
| 2009/0024180 A1 | 1/2009 | Kisker et al. |
| 2009/0048583 A1 | 2/2009 | Williams et al. |
| 2009/0082827 A1 | 3/2009 | Kveen et al. |
| 2009/0082828 A1 | 3/2009 | Ostroff |
| 2009/0171408 A1 | 7/2009 | Solem |
| 2009/0192570 A1 | 7/2009 | Jaax et al. |
| 2009/0198293 A1 | 8/2009 | Cauller et al. |
| 2009/0198295 A1 | 8/2009 | Dennis et al. |
| 2009/0198308 A1 | 8/2009 | Gross et al. |
| 2009/0326601 A1 | 12/2009 | Brisken et al. |
| 2010/0094367 A1 | 4/2010 | Sen |
| 2010/0161002 A1 | 6/2010 | Aghassian et al. |
| 2010/0179628 A1 | 7/2010 | Towe et al. |
| 2010/0249883 A1 | 9/2010 | Zdeblick |
| 2010/0249885 A1 | 9/2010 | Colvin et al. |
| 2010/0286744 A1 | 11/2010 | Echt et al. |
| 2010/0304209 A1 | 12/2010 | Lund et al. |
| 2010/0305627 A1 | 12/2010 | Anderson |
| 2010/0305628 A1 | 12/2010 | Lund et al. |
| 2010/0305629 A1 | 12/2010 | Lund et al. |
| 2010/0312320 A1 | 12/2010 | Faltys et al. |
| 2011/0054555 A1 | 3/2011 | Williams et al. |
| 2011/0060392 A1 | 3/2011 | Zdeblick et al. |
| 2011/0071585 A1 | 3/2011 | Ransbury et al. |
| 2011/0071586 A1 | 3/2011 | Jacobson |
| 2011/0077708 A1 | 3/2011 | Ostroff |
| 2011/0077721 A1 | 3/2011 | Whitehurst et al. |
| 2011/0137378 A1 | 6/2011 | Klosterman et al. |
| 2011/0160801 A1 | 6/2011 | Markowitz et al. |
| 2011/0208260 A1 | 8/2011 | Jacobson |
| 2011/0245782 A1 | 10/2011 | Berthiaume et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0313490 A1 | 12/2011 | Parramon et al. |
| 2012/0059431 A1 | 3/2012 | Williams et al. |
| 2012/0081201 A1 | 4/2012 | Norgaard et al. |
| 2012/0095521 A1 | 4/2012 | Hintz |
| 2012/0095539 A1 | 4/2012 | Khairkhahan et al. |
| 2012/0109149 A1 | 5/2012 | Bonner et al. |
| 2012/0109236 A1 | 5/2012 | Jacobson et al. |
| 2012/0116489 A1 | 5/2012 | Khairkhahan et al. |
| 2012/0143271 A1 | 6/2012 | Root et al. |
| 2012/0158090 A1 | 6/2012 | Chavan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0179219 A1 | 7/2012 | Kisker et al. |
| 2012/0197352 A1 | 8/2012 | Carbunaru et al. |
| 2012/0197373 A1 | 8/2012 | Khairkhahan et al. |
| 2012/0232371 A1 | 9/2012 | Mech et al. |
| 2012/0290021 A1 | 11/2012 | Saurkar et al. |
| 2012/0290025 A1 | 11/2012 | Keimel |
| 2012/0316622 A1 | 12/2012 | Whitehurst et al. |
| 2012/0323099 A1 | 12/2012 | Mothilal et al. |
| 2013/0023975 A1 | 1/2013 | Locsin |
| 2013/0030483 A1 | 1/2013 | Demmer et al. |

(56) References Cited

U.S. PATENT DOCUMENTS

| | | |
|---|---|---|
| 2013/0035748 A1 | 2/2013 | Bonner et al. |
| 2013/0066169 A1 | 3/2013 | Rys et al. |
| 2013/0073004 A1 | 3/2013 | Root et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103109 A1 | 4/2013 | Jacobson |
| 2013/0110127 A1 | 5/2013 | Bornzin et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0123872 A1 | 5/2013 | Bornzin et al. |
| 2013/0123875 A1 | 5/2013 | Varady et al. |
| 2013/0131159 A1 | 5/2013 | Ko et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0184790 A1 | 7/2013 | Schleicher et al. |
| 2013/0226259 A1 | 8/2013 | Penner et al. |
| 2013/0231710 A1 | 9/2013 | Jacobson |
| 2013/0234692 A1 | 9/2013 | Liang et al. |
| 2013/0235663 A1 | 9/2013 | Walsh et al. |
| 2013/0235672 A1 | 9/2013 | Walsh et al. |
| 2013/0238044 A1 | 9/2013 | Penner |
| 2013/0238056 A1 | 9/2013 | Poore et al. |
| 2013/0238072 A1 | 9/2013 | Deterre et al. |
| 2013/0238073 A1 | 9/2013 | Makdissi et al. |
| 2013/0238840 A1 | 9/2013 | Walsh et al. |
| 2013/0253309 A1 | 9/2013 | Allan et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijis et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0302665 A1 | 11/2013 | Zhao et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012342 A1 | 1/2014 | Penner et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0026016 A1 | 1/2014 | Nicholes |
| 2014/0031836 A1 | 1/2014 | Ollivier |
| 2014/0031837 A1 | 1/2014 | Perryman et al. |
| 2014/0039570 A1 | 2/2014 | Carroll et al. |
| 2014/0039578 A1 | 2/2014 | Whitehurst et al. |
| 2014/0039588 A1 | 2/2014 | Ok et al. |
| 2014/0039591 A1 | 2/2014 | Drasler et al. |
| 2014/0046395 A1 | 2/2014 | Regnier et al. |
| 2014/0058240 A1 | 2/2014 | Mothilal et al. |
| 2014/0072872 A1 | 3/2014 | Hodgkinson et al. |
| 2014/0100627 A1 | 4/2014 | Min |
| 2015/0224320 A1* | 8/2015 | Stahmann ............ A61N 1/0587 607/25 |

FOREIGN PATENT DOCUMENTS

| | | |
|---|---|---|
| EP | 1541191 A1 | 6/2005 |
| TW | 1251986 B | 3/2006 |
| TW | 1252007 B | 3/2006 |
| WO | 2006099425 A1 | 9/2006 |
| WO | 2009006531 A1 | 1/2009 |
| WO | 2009052480 A2 | 4/2009 |
| WO | 2012150000 | 11/2012 |
| WO | 2012154599 A2 | 11/2012 |
| WO | 2013080038 A2 | 6/2013 |
| WO | 2014046662 | 3/2014 |

OTHER PUBLICATIONS

US 8,116,861, 02/2012, Root et al. (withdrawn)

* cited by examiner

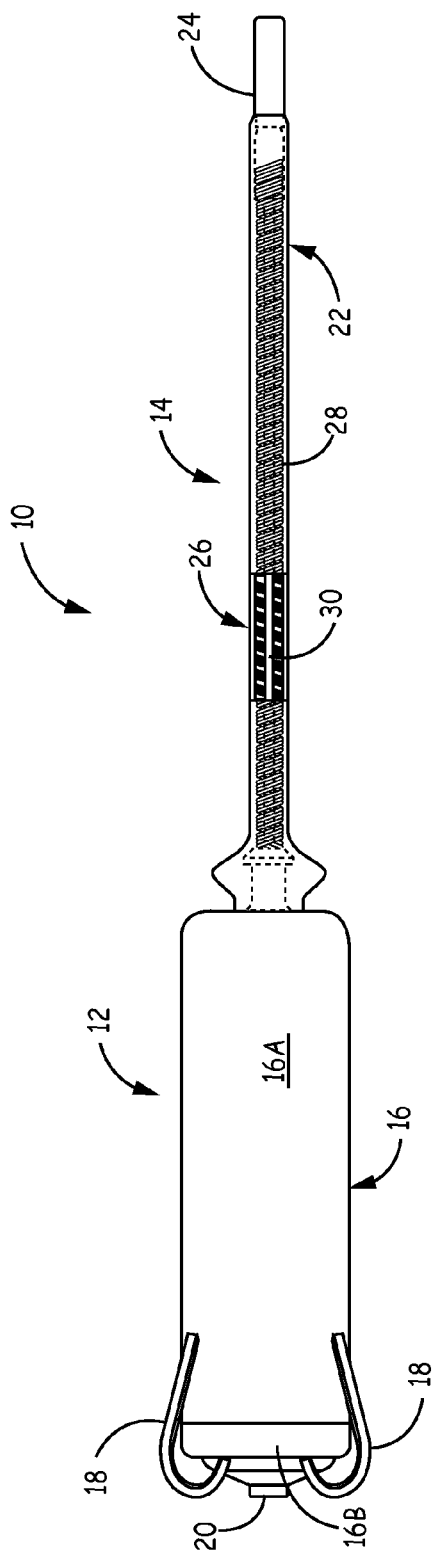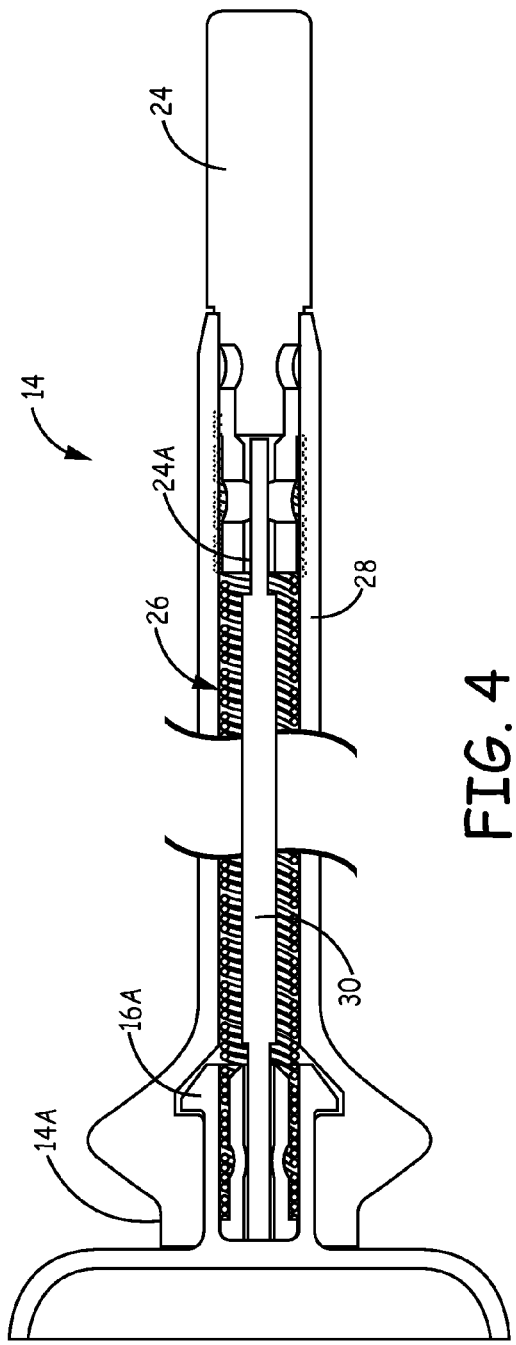

COORDINATION OF VENTRICULAR PACING IN A LEADLESS PACING SYSTEM

TECHNICAL FIELD

The disclosure relates to cardiac pacing, and more particularly, to cardiac pacing using a leadless pacing device.

BACKGROUND

An implantable pacemaker may deliver pacing pulses to a patient's heart and monitor conditions of the patient's heart. In some examples, the implantable pacemaker comprises a pulse generator and one or more electrical leads. The pulse generator may, for example, be implanted in a small pocket in the patient's chest. The electrical leads may be coupled to the pulse generator, which may contain circuitry that generates pacing pulses and/or senses cardiac electrical activity. The electrical leads may extend from the pulse generator to a target site (e.g., an atrium and/or a ventricle) such that electrodes at the distal ends of the electrical leads are positioned at a target site. The pulse generator may provide electrical stimulation to the target site and/or monitor cardiac electrical activity at the target site via the electrodes.

A leadless pacing device has also been proposed for sensing electrical activity and/or delivering therapeutic electrical signals to the heart. The leadless pacing device may include one or more electrodes on its outer housing to deliver therapeutic electrical signals and/or sense intrinsic depolarizations of the heart. The leadless pacing device may be positioned within or outside of the heart and, in some examples, may be anchored to a wall of the heart via a fixation mechanism.

SUMMARY

In general, this disclosure describes techniques for coordinating ventricular pacing with intrinsic depolarizations in another chamber of the heart in an implantable medical system that comprises a leadless pacing device (LPD) implanted on or within a ventricle. In some instances, the leadless pacing device may be unable to detect the intrinsic depolarizations in the other chamber. Accordingly, in some instances, the LPD may be unable to independently provide ventricular pacing that is coordinated with the intrinsic depolarizations of the other chamber.

However, another implantable medical device (IMD) in the implantable medical system may be able to sense the intrinsic depolarizations in the other chamber. The other IMD may deliver an electrical pulse in response to detecting an intrinsic depolarization in the other chamber. The electrical pulse delivered by the other IMD may have a higher amplitude than the intrinsic depolarizations of the other chamber. The LPD may detect the electrical pulse delivered by the other IMD and, in response to detecting the electrical pulse, deliver a pacing pulse to the ventricle via at least a first electrode in coordination with the intrinsic depolarization of the other chamber. In this manner, the LPD may provide ventricular pacing coordinated with the intrinsic activity of the other chamber in instances in which the LPD cannot sense the intrinsic activity of the other chamber.

In one example, an implantable medical system is configured to coordinate ventricular pacing with intrinsic depolarizations of another chamber. The implantable medical system comprises a leadless pacing system that comprises a leadless pacing device, and a sensing extension. The leadless pacing device comprises a stimulation module configured to generate pacing pulses, a sensing module, a processing module, a housing configured to be implanted on or within a ventricle of a heart of a patient, wherein the housing encloses the stimulation module, the sensing module, and the processing module, and a first electrode electrically coupled to the sensing module and the stimulation module. The sensing extension extends from the housing and comprises a body extending from the housing, and a second electrode carried by the body and electrically connected to the sensing module and the stimulation module. The sensing module is configured to sense electrical activity of the ventricle via the first and second electrodes, and the stimulation module is configured to deliver pacing pulses to the ventricle via at least the first electrode. The implantable medical system further comprises another implantable medical device configured to sense an intrinsic depolarization of the other chamber of the heart of the patient and, in response to the intrinsic depolarization of the other chamber, deliver an electrical pulse. The sensing module of the leadless pacing device is configured to detect the electrical pulse delivered by the other implantable medical device via the first electrode and the second electrode. In response to the sensing module of the leadless pacing device detecting the electrical pulse delivered by the other implantable medical device, the processing module of the leadless pacing device is configured to control the stimulation module of the leadless pacing device to generate a pacing pulse for delivery to the ventricle via at least the first electrode in coordination with the intrinsic depolarization of the other chamber.

In another example, an implantable medical system is configured to provide atrio-synchronous ventricular pacing. The implantable medical system comprises a leadless pacing system comprising a first leadless pacing device and a sensing extension. The first leadless pacing device comprises a first stimulation module configured to generate pacing pulses, a first sensing module, a first processing module, a first housing configured to be implanted within a right ventricle of a heart of a patient, wherein the first housing encloses the first stimulation module, the first sensing module, and the first processing module, and a first electrode electrically coupled to the first sensing module and the first stimulation module. The sensing extension extends from the first housing and comprises a body extending from the first housing, and a second electrode carried by the body and electrically connected to the first sensing module and the first stimulation module. The first sensing module is configured to sense electrical activity of the right ventricle via the first and second electrodes, and the first stimulation module is configured to deliver pacing pulses to the right ventricle via at least the first electrode. The implantable medical system further comprises a second leadless pacing device comprising a second a stimulation module configured to generate pacing pulses, a second a sensing module, a second processing module, and a second housing configured to be implanted within a right atrium of the heart of the patient, wherein the second housing encloses the second stimulation module, the second sensing module, and the second processing module, and wherein the second housing comprises a third electrode and a fourth electrode. The second sensing module of the second leadless pacing device is configured to detect an intrinsic depolarization of the atrium via the third electrode and the fourth electrode. The second stimulation module of the second leadless pacing device is configured to generate pacing pulses. In response to the second sensing module detecting the intrinsic depolarization of the atrium, the second processing module of the second leadless pacing device is configured to control the second stimulation module of the second leadless pacing device to deliver a pacing pulse via the third electrode and the fourth electrode during a refractory period of the right atrium following the intrinsic depolarization of the right atrium. The first sensing module of the first leadless pacing device is configured to detect, via the first electrode and the second electrode, the pacing pulse delivered by the second leadless pacing device and, in response to the first sensing module of the first leadless pacing device detecting the pacing pulse delivered by the second leadless pacing device, the first processing module of the first leadless pacing device is configured to control the first stimulation module of the first leadless pacing device to generate a pacing pulse for delivery to the right ventricle via at least the first electrode an atrio-ventricular (AV) delay interval after the first sensing module detected the pacing pulse delivered by the second leadless pacing device.

In another example, a method for coordinating ventricular pacing by a leadless pacing system with intrinsic depolarizations of another chamber is described. The leadless pacing system comprises a leadless pacing device, and a sensing extension. The leadless pacing device comprises a stimulation module configured to generate pacing pulses, a sensing module, a processing module, a housing configured to be implanted on or within a ventricle of a heart of a patient, wherein the housing encloses the stimulation module, the sensing module, and the processing module, and a first electrode electrically coupled to the sensing module and the stimulation module. The sensing extension extends from the housing and comprises a body extending from the housing, and a second electrode carried by the body and electrically connected to the sensing module and the stimulation module. The sensing module is configured to sense electrical activity of the ventricle via the first and second electrodes, and the stimulation module is configured to deliver pacing pulses to the ventricle via at least the first electrode. The method comprises sensing, by another implantable medical device an intrinsic depolarization of the other chamber of the heart of the patient and, in response to the intrinsic depolarization of the other chamber, delivering, by the other implantable medical device, an electrical pulse. The method further comprises detecting, by the sensing module of the leadless pacing device, the electrical pulse delivered by the other implantable medical device via the first electrode and the second electrode and, in response detecting the electrical pulse delivered by the other implantable medical device, delivering, by the stimulation module of the leadless pacing device, a pacing pulse to the ventricle via at least the first electrode in coordination with the intrinsic depolarization of the other chamber.

In another aspect, the disclosure is directed to a computer-readable storage medium comprising computer-readable instructions for execution by a processor. The instructions cause a programmable processor to perform any whole or part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. In some examples, the computer-readable medium is an article of manufacture and is non-transitory.

The details of one or more examples are set forth in the accompanying drawings and the description below. Other features, objects, and advantages will be apparent from the description and drawings, and from the claims.

BRIEF DESCRIPTION OF THE DRAWINGS

FIG. 3 illustrates an example leadless pacing system that comprises a leadless pacing device and a sensing extension.

FIG. 4 is a schematic cross-sectional view of the sensing extension of FIG. 1.

DETAILED DESCRIPTION

Figure 1:
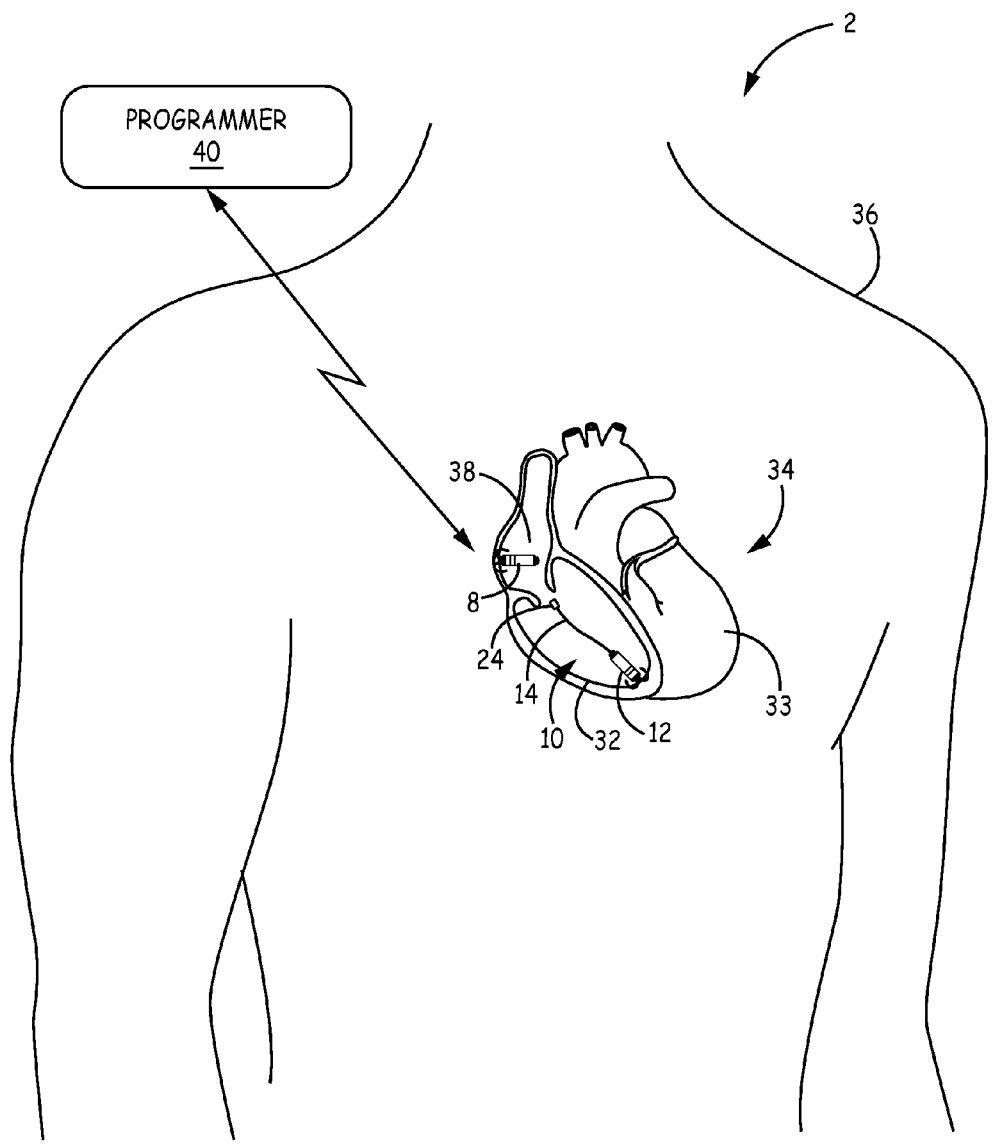
FIG. 1 is a conceptual illustration of an example medical device system that includes a leadless pacing system and another implanted medical device.

Typically, dual-chamber implantable pacemakers are implanted within a pocket within the patient's chest, and coupled to a right-atrial lead and a right-ventricular lead. The right-atrial lead extends from the implantable pacemaker in the pocket to the right atrium of the patient's heart, and positions one or more electrodes within the right atrium. The right-ventricular lead extends from the implantable pacemaker in the pocket to the right ventricle of the patient's heart, and positions one or more electrodes within the right ventricle.

Such dual-chamber implantable pacemakers sense respective cardiac electrical activity, e.g., respective cardiac electrograms, via the one or more electrodes implanted within the right atrium and the one or more electrodes implanted within the right ventricle. In particular, such dual-chamber implantable pacemakers detect intrinsic atrial depolarizations via the one or more electrodes implanted within the right atrium, and intrinsic ventricular depolarizations via the one or more electrodes implanted within the right ventricle. The implantable pacemakers may also deliver pacing pulses to the right atrium and the right ventricle via the one or more electrodes in the right atrium and the right ventricle, respectively. Due to the ability to sense both atrial and ventricular electrical activity, such dual-chamber implantable pacemakers may be able to provide atrio-synchronous ventricular pacing. For patients with intermittent AV node conduction, it may be preferable to inhibit ventricular pacing and allow an intrinsic ventricular depolarization to occur for a time, referred to as the AV interval, after an intrinsic atrial depolarization or atrial pace. Such atrio-synchronous pacing in dual-chamber implantable pacemakers is referred to as the VDD programming mode, and may be used for patients with various degrees of AV block.

Implantable cardiac leads and the pocket in which pacemakers are implanted may be associated with complications. To avoid such complications, LPDs sized to be implanted entirely within one chamber, e.g., the right ventricle, of the heart have been proposed. Some proposed LPDs include a plurality of electrodes that are affixed to, or are a portion of, the housing of the LPD.

Some proposed LPDs are capable of sensing intrinsic depolarizations of, and delivering pacing pulses to, the chamber of the heart in which they are implanted via the plurality of electrodes. However, because they are not coupled to electrodes in any other chamber, some proposed LPDs are incapable of sensing intrinsic depolarizations of, and delivering pacing pulses to, another chamber of the heart. Consequently, when implanted in the right ventricle, for example, such proposed LPDs may be unable to sense intrinsic atrial depolarizations of the atria, and may be limited to delivery of ventricular pacing according to an asynchronous ventricular pacing, e.g., according to mode that corresponds to a VVI or VVIR mode of a dual-chamber pacemaker.

This disclosure describes techniques for coordinating ventricular pacing with intrinsic depolarizations in another chamber of the heart in an implantable medical system that comprises a ventricular LPD that may be unable to detect the intrinsic depolarizations in the other chamber, and may be unable to independently provide ventricular pacing that is coordinated with the intrinsic depolarizations of the other chamber. Another IMD in the implantable medical system may be able to sense the intrinsic depolarizations in the other chamber. The other IMD may deliver an electrical pulse in response to detecting an intrinsic depolarization in the other chamber. The electrical pulse delivered by the other IMD may have a higher amplitude than the intrinsic depolarizations of the other chamber. Consequently, the amplitude of the electrical pulse as sensed by the LPD may be higher than the amplitude of the intrinsic depolarizations of the other chamber at the LPD, which the LPD may not be able to sense. As an example, the amplitude of the electrical pulse as sensed by the LPD may be approximately 1.2 millivolts (mV). The LPD may detect the electrical pulse delivered by the other IMD and, in response to detecting the electrical pulse, deliver a pacing pulse to the ventricle via at least the first electrode in coordination with the intrinsic depolarization of the other chamber. In this manner, the LPD may provide ventricular pacing coordinated with the intrinsic activity of the other chamber in instances in which the LPD cannot sense the intrinsic activity of the other chamber.

In some examples, the LPD is part of a leadless pacing system that also includes a sensing extension extending from a housing of the LPD. The sensing extension includes one or more electrodes with which the LPD may sense electrical cardiac activity, and also sense the electrical pulse delivered by the other IMD. In some examples, the LPD senses the electrical pulses delivered by the other LPD via one electrode on its housing and another electrode on the sensing extension. The relatively greater spacing between these electrodes may increase the ability of the LPD to detect the electrical pulses relative to two more closely spaced electrodes, e.g., on the LPD housing. The amplitude of the electrical pulse as sensed by the LPD may be dependent on the relative position and orientation of the electrodes used by the LPD sense the electrical pulse, and the electrodes used by the other IMD to deliver the electrical pulse. The relatively greater electrode spacing and the electrode orientation provided by an LPD coupled to a sensing extension may result in an increased amplitude of the electrical pulse as sensed by the LPD, which may make it easier for the LPD to detect the electrical pulses delivered by the other IMD.

Increased amplitude of the electrical pulse as sensed by the LPD may also be achieved by increasing the spacing and/or selecting a preferable orientation of the electrodes used by the other IMD to deliver the electrical pulse. For example, the other IMD may deliver the electrical pulse using a unipolar electrode vector, e.g., including a lead-borne electrode and an electrode on the housing of the other IMD. As another example, if the other IMD is another LPD, the other LPD may be coupled to a sensing extension, and deliver the electrical pulses via an electrode vector that includes an electrode on the sensing extension. A user of the medical device system, or the other IMD automatically, may vary the electrode vector used by the other IMD to deliver the electrical pulses to optimize the detection of the electrical pulse by the LPD.

In some examples, the LPD is configured to be implanted within a first chamber (e.g., a ventricle) of a heart of a patient, and the sensing extension is configured to position one or more electrodes proximate a second chamber of the heart. For example, the sensing extension may have a length selected to position the one or more electrodes of the sensing extension adjacent the right atrium when the LPD is implanted in or near the apex of the right ventricle. The one or more electrodes of the sensing extension may be used to sense intrinsic ventricular electrical activity, as well as detect electrical pulses delivered by another IMD to indicate intrinsic depolarization of another chamber.

In some examples, the sensing extension includes a self-supporting body configured to passively (i.e., without any active fixation elements, such as tines or a fixation helix) position an electrode extension at a location away from the LPD. The self-supporting body may be flexible enough to reduce irritation to the tissue of the heart when the body contacts the tissue, but have sufficient rigidity to permit the sensing extension to extend away from the LPD housing and towards the second chamber, even in the presence of blood in the first chamber of the heart. The stiffness of the self-supporting body is selected to help prevent the body from collapsing in on itself and/or towards the LPD, e.g., in the presence of blood flow. In addition, the stiffness of the self-supporting body may be selected so that the body is configured to support its own weight, e.g., in the presence of gravity.

In some examples, the other chamber is an atrium of the heart, and the LPD provides atrio-synchronous ventricular pacing in response to detecting the electrical pulse from the other IMD. In some examples, the LPD delivers the ventricular pacing pulse an atrio-ventricular (AV) delay interval after detecting the electrical pulse delivered by the other IMD. In this manner, the implantable medical system may be able to provide pacing according to a VDD or DDD pacing mode. In some examples, the LPD may provide rate-responsive cardiac pacing, e.g., by adjusting the AV delay interval based on one or more patient parameters indicative of demand, such as activity sensed via an accelerometer and/or respiration. In some examples, the LPD may adjust the AV delay interval based on changes in an atrial rate indicated by intervals between consecutive electrical pulses from the other IMD.

In some examples, the other chamber is another ventricle of the heart. In such examples, the LPD may deliver the pacing pulse to the ventricle a ventricular-ventricular (VV) delay interval after detecting the electrical pulse delivered by the other IMD that indicates intrinsic depolarization of the other ventricle. In this manner, the implantable medical system may provide cardiac resynchronization therapy (CRT), which may include bi-ventricular pacing.

FIG. 1 is a conceptual illustration of an example implantable medical system 2 that includes a leadless pacing system 10 and another IMD. Leadless pacing system 10 includes an LPD 12 and sensing extension 14. In the example of FIG. 1, leadless pacing system 10 is implanted in right ventricle 32 of heart 34 of patient 36. In the illustrated example, the other IMD is another LPD 8 implanted in the right atrium 38 of heart 34.

Implantable medical system 2 is an example of an implantable medical system configured to coordinate the delivery of ventricular pacing with intrinsic depolarizations of another chamber of the heart. Because LPD 8 is configured to sense intrinsic depolarizations of an atrium, e.g., right atrium 38, implantable medical system 2 is an example of an implantable medical system configured to provide atrio-synchronous ventricular pacing. LPD 8 detects intrinsic depolarizations of atrium 38 and, in response to detecting the intrinsic depolarization of the atrium, delivers an electrical pulse, which may be a pacing pulse delivered during a refractory period of atrium 38 following the intrinsic depolarization of the atrium. LPD 12 is configured to detect, e.g., via electrode 24 on sensing extension 14, the pacing pulse delivered by LPD 8. In response to detecting the electrical pulse from the LPD 8, LPD 12 delivers a pacing pulse to right ventricle 32 in coordination with the intrinsic depolarization of right atrium 38. In some examples, LPD 12 delivers the pacing pulse an AV delay interval after detected the electrical pulse from LPD 8, and thereby provides atrio-synchronous ventricular pacing.

In the example shown in FIG. 1, sensing extension 14 is configured to extend away from LPD 12 and towards right atrium 38 when LPD 12 is implanted in an apex of right ventricle 32. In some examples, sensing extension 14 may have a length that permits sensing extension 14 to remain in right ventricle 32 with LPD 12, as shown in FIG. 1. For example, sensing extension 14 may have a length of about 60 millimeters (as measured from the proximal end connected to LPD 12 and a distal end of electrode 24).

In some examples, rather than being affixed to cardiac tissue such that electrode 24 is in direct contact with heart 34, a distal portion of sensing extension 14 is passive, such that sensing extension 14 may move within right ventricle 32. In some examples, sensing extension 14 may be self-supporting, such that sensing extension 14 is nevertheless configured to continue to extend away from LPD 12 and towards right atrium 38, even in the presence of blood flow from right atrium 38 to right ventricle 32. Providing some flexibility in sensing extension 14 may enable sensing extension 14 to minimize interference with blood flow in right ventricle 32 (or another chamber if LPD 12 is implanted in another chamber).

Also shown in FIG. 1 is medical device programmer 40, which is configured to program, and retrieve data from, LPD 8 and LPD 12. Programmer 40 may be a handheld computing device, desktop computing device, a networked computing device, etc. Programmer 40 may include a computer-readable storage medium having instructions that cause a processor of programmer 40 to provide the functions attributed to programmer 40 in the present disclosure. LPD 8 and LPD 12 may wirelessly communicate with programmer 40. For example, LPD 8 and LPD 12 may transfer data to programmer 40 and may receive data from programmer 40. Programmer 40 may also wirelessly program and/or wirelessly charge LPD 8 and LPD 12.

Data retrieved from LPD 8 and LPD 12 using programmer 40 may include cardiac EGMs stored by the LPDs that indicate electrical activity of heart 34 and marker channel data that indicates the occurrence and timing of sensing, diagnosis, and therapy events associated with LPD 8 and LPD 12. Data transferred to LPD 8 and LPD 12 using programmer 40 may include, for example, operational programs for the LPDs that cause the LPDs to operate as described herein. Data transferred to the LPDs may include any programmable parameters of the LPDs or other IMDs described herein, such as the lengths of any intervals or delays described herein, the width and/or amplitude of the electrical pulses delivered by the other IMD, such as LPD 8, and the electrode vectors used by the IMDs to deliver and sense electrical pulses indicative of intrinsic depolarization of another chamber.

Although described herein primarily with respect to the example implantable medical system 2 of FIG. 1, which includes an LPD 12 implanted within right ventricle 32 and an LPD 8 implanted in right atrium 38, the techniques for coordinating delivery of ventricular pacing with intrinsic depolarizations of another chamber of the heart described herein may be implemented in any of a variety of implantable medical systems including any of a variety of IMDs. In some implantable medical device systems, LPD 8 may be replaced by any IMD capable of sensing intrinsic atrial depolarizations and delivering electrical pulses. For example, some implantable medical device systems may include any single chamber atrial pacemaker, e.g., capable of operating according to an AAI pacing mode, such as a leaded atrial pacemaker. The atrial pacemaker may sense an atrial depolarization, and deliver a pacing pulse immediately or a short interval after sensing the depolarization, e.g., during the atrial refractory period. LPD 12 may detect the artifact of the pacing pulse from the atrial pacemaker, and deliver a pacing pulse to right ventricle 32 a delay interval, e.g., an AV delay interval, after detecting the pacing artifact. In this manner, an implantable medical system including LPD 12 and the atrial pacemaker may collectively function as a dual chamber, e.g., VDD or DDD, pacemaker without a right ventricular lead.

In some examples, LPD 12 need not be implanted in right ventricle 32. In some examples, LPD 12 may be implanted on or within the left ventricle 33, and the other IMD may be an LPD implanted on or within right ventricle 32, or a leaded ventricular pacemaker, such as a single-chamber ventricular pacemaker coupled to a lead that extends to right ventricle 32, or a dual-chamber pacemaker or implantable cardioverter-defibrillator (ICD) coupled to leads that extend to right ventricle 32 and right atrium 38. The ventricular pacemaker may sense an intrinsic depolarization of right ventricle 32, and deliver a pacing pulse immediately or a short interval after sensing the depolarization, e.g., during the refractory period of right ventricle 32. LPD 12 may detect the artifact of the pacing pulse from the ventricular pacemaker, and deliver a pacing pulse to left ventricle 33 upon, or a delay interval after, e.g., a VV delay interval after, detecting the pacing artifact. In this manner, an implantable medical system including LPD 12 and the right ventricular pacemaker may collectively provide CRT. In some examples, LPD 12 may be implanted within any chamber of heart 34, and the other IMD may be any IMD capable of sensing intrinsic depolarizations in another chamber and delivering electrical pulses, such as any cardiac pacemaker, leaded ICD, subcutaneous ICD (SICD), implantable loop recorder, or neurostimulator.

Figure 2:
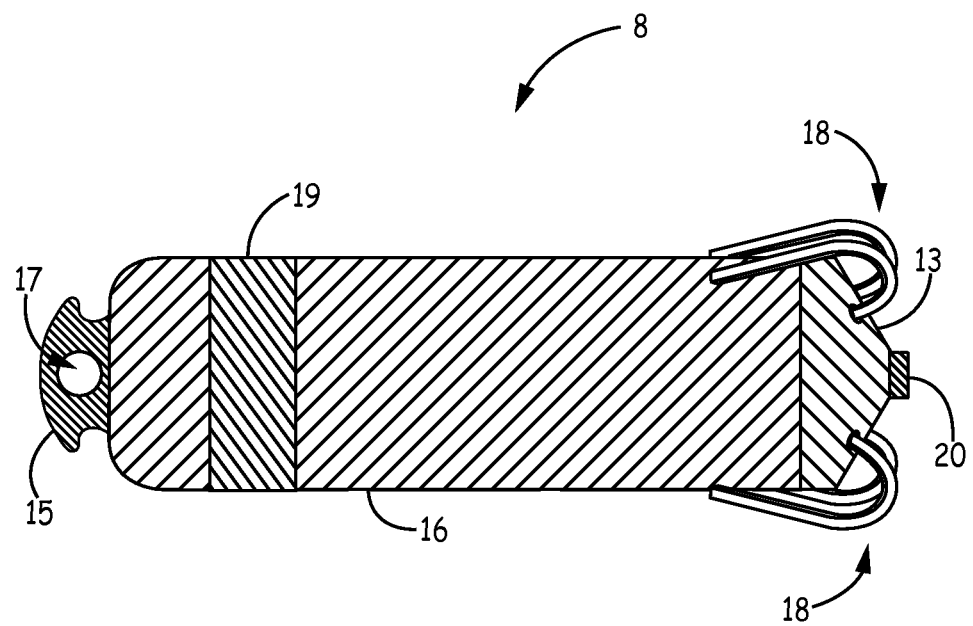
FIG. 2 illustrates an example leadless pacing device.

FIG. 2 is a conceptual drawing illustrating LPD 8 of FIG. 1. As shown in FIG. 2, LPD 8 includes case 16, cap 13, electrode 19, electrode 20, fixation mechanisms 18, and flange 15 defining opening 17. Together, case 16 and cap 13 may be considered the housing of LPD 8. In this manner, case 16 and cap 13 may enclose and protect the various electrical components within LPD 8. Case 16 may enclose substantially all of the electrical components, and cap 13 may seal case 16 and create the hermetically sealed housing of LPD 8. LPD 8 may typically include at least two electrodes (e.g., electrodes 19 and 20) to deliver an electrical signal (e.g., therapy such as antitachycardia pacing (ATP) or other cardiac pacing, and/or electrical pulses for indicating intrinsic depolarizations) and/or provide at least one sensing vector for sensing a cardiac electrogram).

Electrodes 19 and 20 are carried on the housing created by case 16 and cap 13. In this manner, electrodes 19 and 20 may be considered leadless electrodes. In the example of FIG. 2, electrode 20 is disposed on the exterior surface of cap 13. In some examples, electrode 20 may be a circular electrode positioned to contact cardiac tissue upon implantation, and may be referred to as a tip electrode. Electrode 19 may be a ring or cylindrical electrode disposed on the exterior surface of case 16. Other configurations of electrodes 19, 20 may also be used. Both case 16 and cap 13 may be electrically insulating.

Electrode 20 may be used as a cathode and electrode 19 may be used as an anode, or vice versa, for cardiac pacing therapy, such as ATP or post-shock pacing, or delivering electrical pulses to indicate intrinsic depolarizations. In addition, electrodes 19 and 20 may be used to detect intrinsic electrical signals from cardiac muscle, such as intrinsic depolarizations of a cardiac chamber, e.g., right atrium 38 (FIG. 1). In other examples, LPD 8 may include three or more electrodes, where any two or more of the electrodes may form a vector for delivery of electrical pulses and detecting intrinsic depolarizations.

Fixation mechanisms 18 may be configured to attach LPD 8 to cardiac tissue. Fixation mechanisms 18 may be active fixation tines, screws, clamps, adhesive members, or any other types of attaching a device to tissue. As shown in the example of FIG. 2, fixation mechanisms 18 may be constructed of a memory material that retains a preformed shape. During implantation, fixation mechanisms 18 may be flexed forward to pierce tissue and allowed to flex back towards case 16. In this manner, fixation mechanisms 18 may be embedded within the target tissue.

Flange 15 may be provided on one end of case 16 to enable tethering or extraction of LPD 8. For example, a suture or other device may be inserted around flange 15 and/or through opening 17 and attached to tissue. In this manner, flange 15 may provide a secondary attachment structure to tether or retain LPD 8 within heart 34 if fixation mechanisms 18 fail. Flange 15 and/or opening 17 may also be used to extract LPD 8 once the LPD needs to be explanted (or removed) from patient 36 if such action is deemed necessary.

FIG. 3 is a conceptual diagram illustrating example leadless pacing system 10 of FIG. 1, which includes LPD 12 and sensing extension 14. LPD 12 is configured to be implanted within a chamber of a heart of a patient, e.g., to monitor electrical activity of the heart and/or provide electrical therapy to the heart. LPD 12 may be similar to LPD 8. For example, in the example shown in FIG. 3, LPD 12 includes outer housing 16, a plurality of fixation tines 18, and electrode 20, which may be substantially the same as the like numbered components of LPD 8 in FIG. 2. However, unlike LPD 8, LPD 12 does not include electrode 19, and is coupled to sensing extension 14. Sensing extension 14 includes self-supporting body 22, electrode 24, and conductor 26.

LPD 12 is configured to sense electrical activity of the heart and deliver electrical stimulation to the heart via electrodes 20, 24. LPD 12 is also configured to sense electrical pulses delivered by another IMD, such as LPD 8, via electrodes 20, 24. LPD 12 comprises electrode 20 and sensing extension 14 comprises electrode 24. For example, electrode 20 may be mechanically connected to housing 16. As another example, electrode 20 may be defined by an outer portion of housing 16 that is electrically conductive. Fixation tines 18 may be configured to anchor LPD 12 to cardiac tissue such that electrode 20 maintains contact with the cardiac tissue.

Sensing extension 14 is configured to position electrode 24 proximate a chamber other than the one in which LPD 12 is implanted. In this way, sensing extension 24 may extend the sensing capabilities of system 10. In the example shown in FIG. 3, electrode 24 is carried by self-supporting body 22 of sensing extension 14, and is located at a distal end of body 22. In other examples, however, electrode 24 may have another position relative to body 22, such mid-way between housing 16 and the distal end of body 22, or otherwise away from the distal end of body 22. Electrode 24 may have any suitable configuration. For example, electrode 24 may have a ring-shaped configuration, or a partial-ring configuration. Electrode 24 may be formed from any suitable material, such as a titanium nitride coated metal. In other examples, system 10 may include more than two electrodes. For example, LPD 12 and/or sensing extension 14 may have more than one electrode.

In the example shown in FIG. 3, electrode 24 is electrically connected to at least some electronics of LPD 12 (e.g., a sensing module and a stimulation module) via electrical conductor 26 of sensing extension 14 and electrically conductive portion 16A of housing 16. Electrical conductor 26 may be electrically connected to and extends between conductive portion 16A of housing 16 and electrode 24. Conductive portion 16A is electrically isolated from electrode 20, but is electrically connected to electrode 24, such that conductive portion 16A and electrode 24 have the same polarity and are electrically common. For example, electrode 20 may be carried by second portion 16B of housing 16, which is electrically isolated from conductive portion 16A. Conductive portion 16A of housing 16 is electrically connected to at least some electronics of LPD 12 (e.g., a sensing module, an electrical stimulation module, or both), such that conductive portion 16A defines part of an electrically conductive pathway from electrode 24 to the electronics. In some examples, conductive portion 16A may define at least a part of a power source case of LPD 12. The power source case may house a power source (e.g., a battery) of LPD 12.

In some examples, conductive portion 16A is substantially completely electrically insulated (e.g., completely electrically insulated or nearly completely electrically insulated. Substantially completely electrically insulating conductive portion 16A may help a sensing module of LPD 12 sense electrical pulses delivered by another IMD with electrode 24 of sensing extension 14. In other examples, however, at least a part of conductive portion 16A may be exposed to define one or more electrodes, which have the same polarity as electrode 24.

As shown in FIG. 4, which is a schematic cross-sectional view of sensing extension 14 and a part of that conductive portion 16A of housing 16, in some examples, conductor 26 may be coiled around conductive portion 16A to establish an electrical connection between conductor 26 and conductive portion 16A. In other examples, however, an electrical connection between conductor 26 and conductive portion 16A may be established using another configuration. For example, conductor 26 may not be coiled within sensing extension 14 and may be crimped or otherwise placed in contact with conductive portion 16A near proximal end 14A of sensing extension 14.

FIG. 4 also illustrates an example electrical connection between electrode 24 and conductor 26. In particular, FIG. 2 illustrates an example in which a distal portion of conductor 26 is crimped to a proximal portion of electrode 24, the proximal portion including proximal end 24A. In other examples, electrode 24 and conductor 26 may be electrically connected using another configuration.

In the example shown in FIGS. 3 and 4, self-supporting body 22 of sensing extension 14 extends between housing 16 and electrode 24. Self-supporting body 22 may have a stiffness that permits body 22 to substantially maintain (e.g., completely maintain or nearly maintain) its position relative to LPD 12, or at least the position of electrode 24 relative to LPD 12, even in the presence of gravity and in the presence of blood flow in the heart. Self-supporting body 22 is configured to passively position electrode 24 at a location away from LPD 12, e.g., proximate or within a chamber of the heart other than the one in which LPD 12 is implanted. For example, self-supporting body 22 may have sufficient rigidity to permit sensing extension 14 to extend away from housing 16, even as the sensing extension moves within blood in the chamber of the heart. In addition, self-supporting body 22 may be flexible enough to minimize irritation to the tissue of the heart, should body 22 contact the tissue.

In the example shown in FIGS. 3 and 4, electrical conductor 26 is covered by an electrically insulative material, such as a polymer (e.g., polyurethane) or silicone. For example, conductor 26 may be housed within a polyurethane or silicone sleeve 28, as shown in FIGS. 3 and 4. In some cases, coiled conductor 26 may not provide sufficient stiffness to sensing extension 14 to enable self-supporting body 22 to substantially maintain its position relative to LPD 12 in the presence of blood flow in the heart. Thus, in some examples, sensing extension 14 may also include a stiffness member 30, which has a higher stiffness than coiled conductor 26 (when coiled). In the example shown in FIGS. 3 and 4, self-supporting body 22 of sensing extension 14 is defined by conductor 26, sleeve 28, and stiffness member 30.

Figure 5:
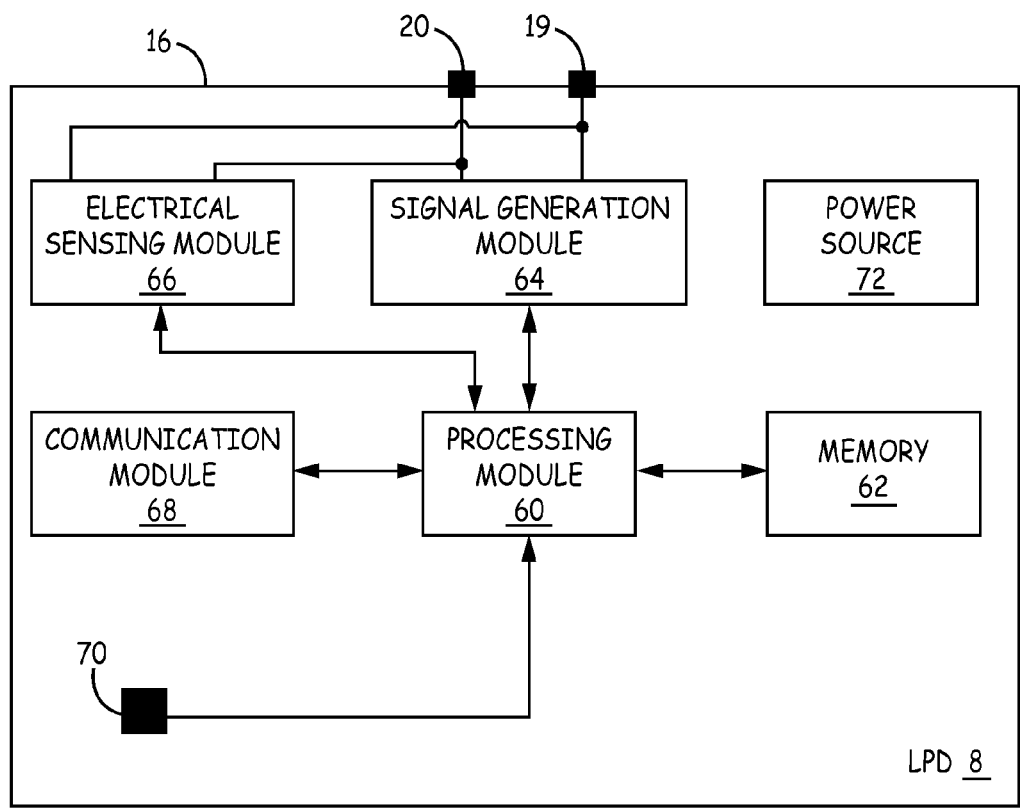
FIG. 5 is a functional block diagram illustrating an example configuration of the leadless pacing device of FIG. 1.

FIG. 5 is a functional block diagram illustrating an example configuration of LPD 8. LPD 8 includes a processing module 60, memory 62, signal generation module 64, electrical sensing module 66, communication module 68, sensor 70, and power source 72. Power source 72 may include a battery, e.g., a rechargeable or non-rechargeable battery.

Modules included in LPD 8 represent functionality that may be included in LPD 8 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, and the like. The functions attributed to the modules herein may be embodied as one or more processors, hardware, firmware, software, or any combination thereof. Depiction of different features as modules is intended to highlight different functional aspects, and does not necessarily imply that such modules must be realized by separate hardware or software components. Rather, functionality associated with one or more modules may be performed by separate hardware or software components, or integrated within common or separate hardware or software components.

Processing module 60 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry.

Processing module 60 may communicate with memory 62. Memory 62 may include computer-readable instructions that, when executed by processing module 60, cause processing module 60 to perform the various functions attributed to processing module 60 herein. Memory 62 may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory 62 may include instructions that, when executed by one or more processors, cause the modules to perform various functions attributed to the modules herein. For example, memory 62 may include pacing instructions and values for any intervals, delays pulse amplitudes, pulse widths, or the like described herein. The pacing instructions and values may be updated by programmer 40 (FIG. 1).

Signal generation module 64 and electrical sensing module 66 are electrically coupled to electrodes 19, 20. Processing module 60 is configured to control signal generation module 64 to generate and deliver electrical pulses, or other signals, via electrodes 19, 20. The electrical pulses may include electrical pulses to signal intrinsic depolarizations of a chamber of heart 34, e.g., right atrium 38, and pacing pulses to stimulate the chamber, e.g., the right atrium.

In addition, processing module 60 is configured to control electrical sensing module 66 monitor signals from electrodes 19, 20 in order to monitor electrical activity of heart 34, e.g., right atrium 38. Electrical sensing module 66 may include circuits that acquire electrical signals. Electrical signals acquired by electrical sensing module 66 may include intrinsic cardiac electrical activity, such as intrinsic atrial depolarizations and/or intrinsic ventricular depolarizations. Electrical sensing module 66 may filter, amplify, and digitize the acquired electrical signals to generate raw digital data. Processing module 60 may receive the digitized data generated by electrical sensing module 66. In some examples, processing module 60 may perform various digital signal processing operations on the raw data, such as digital filtering. Processing module 60 may sense cardiac events based on data or signals received from electrical sensing module 66. For example, in examples in which LPD 8 is implanted in right atrium 8, processing module 60 may sense intrinsic atrial depolarizations, e.g., P-waves, based on data or signals received from electrical sensing module 66.

In some examples, in addition to electrical sensing module 66, LPD 8 includes sensor 70, which may comprise at least one of a variety of different sensors. For example, sensor 70 may comprise at least one of a pressure sensor and an accelerometer. Sensor 70 may generate signals that indicate at least one of parameter of patient 12, such as, but not limited to, at least one of: an activity level of patient 36, a hemodynamic pressure, and heart sounds.

Communication module 68 may include any suitable hardware (e.g., an antenna), firmware, software, or any combination thereof for communicating with another device, such as programmer 40 (FIG. 3) or a patient monitor. Under the control of processing module 60, communication module 68 may receive downlink telemetry from and send uplink telemetry to other devices, such as programmer 40 or a patient monitor, with the aid of an antenna included in communication module 68.

Figure 6:
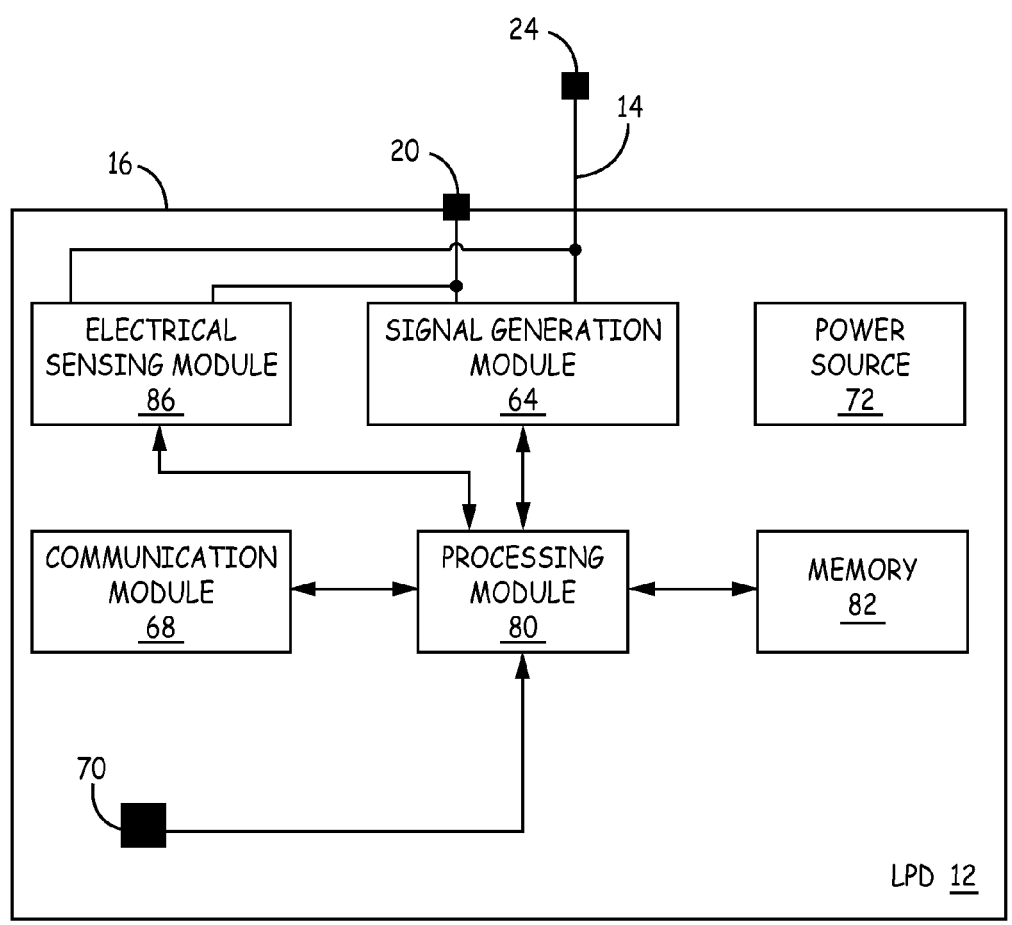
FIG. 6 is a functional block diagram illustrating an example configuration of the leadless pacing system of FIG. 1.

FIG. 6 is a functional block diagram illustrating an example configuration of leadless pacing system 10 (FIG. 1) including LPD 12 and sensing extension 14. LPD 12 includes a processing module 80, memory 82, signal generation module 64, electrical sensing module 86, communication module 68, sensor 70, and power source 72. Signal generation module 64, communication module 68, sensor 70, and power source 72 of LPD 12 are substantially similar to the like numbered modules described above with respect to LPD 8 and FIG. 5. Furthermore, processing module 80, memory 82, and electrical sensing module 86 of LPD 12 may be substantially similar to and provide any of the functionality described above with respect to processing module 60, memory 62, and electrical sensing module 66 of LPD 8, described with respect to FIG. 5.

Signal generation module 64 and electrical sensing module 86 are electrically coupled to electrodes 20, 24. Processing module 80 is configured to control signal generation module 64 to generate and deliver electrical pulses, or other signals, via electrodes 20, 24. The electrical pulses may include pacing pulses to stimulate the chamber in which LPD 12 and sensing extension 14 are implanted, e.g., right ventricle 32.

Processing module 80 is also configured to control electrical sensing module 86 monitor signals from electrodes 20, 24 in order to monitor electrical activity of heart 34, e.g., to detect intrinsic depolarizations of right ventricle 32, such as by detecting R-waves. In addition, processing module 80 is configured to control electrical sensing module 86 to monitor signals from electrodes 20, 24 in order to detect electrical pulses delivered by another IMD, e.g., LPD 8, to indicated an intrinsic depolarizations of another chamber of heart 34, e.g., right atrium 38. In response to detecting the electrical pulse delivered by the other IMD, processing module 80 is configured to control stimulation module 64 to deliver a pacing pulse to the chamber in which LPD 12 is implanted, e.g., right ventricle 32. Processing module 80 may be configured to control signal generation module 64 to deliver the pacing pulse a predetermined interval, e.g., an AV interval, after detecting the pulse delivered by the other IMD. In this manner, in some examples, processing module 80 may be configured to control LPD 12 to provide atrio-synchronous ventricular pacing.

Figure 7:
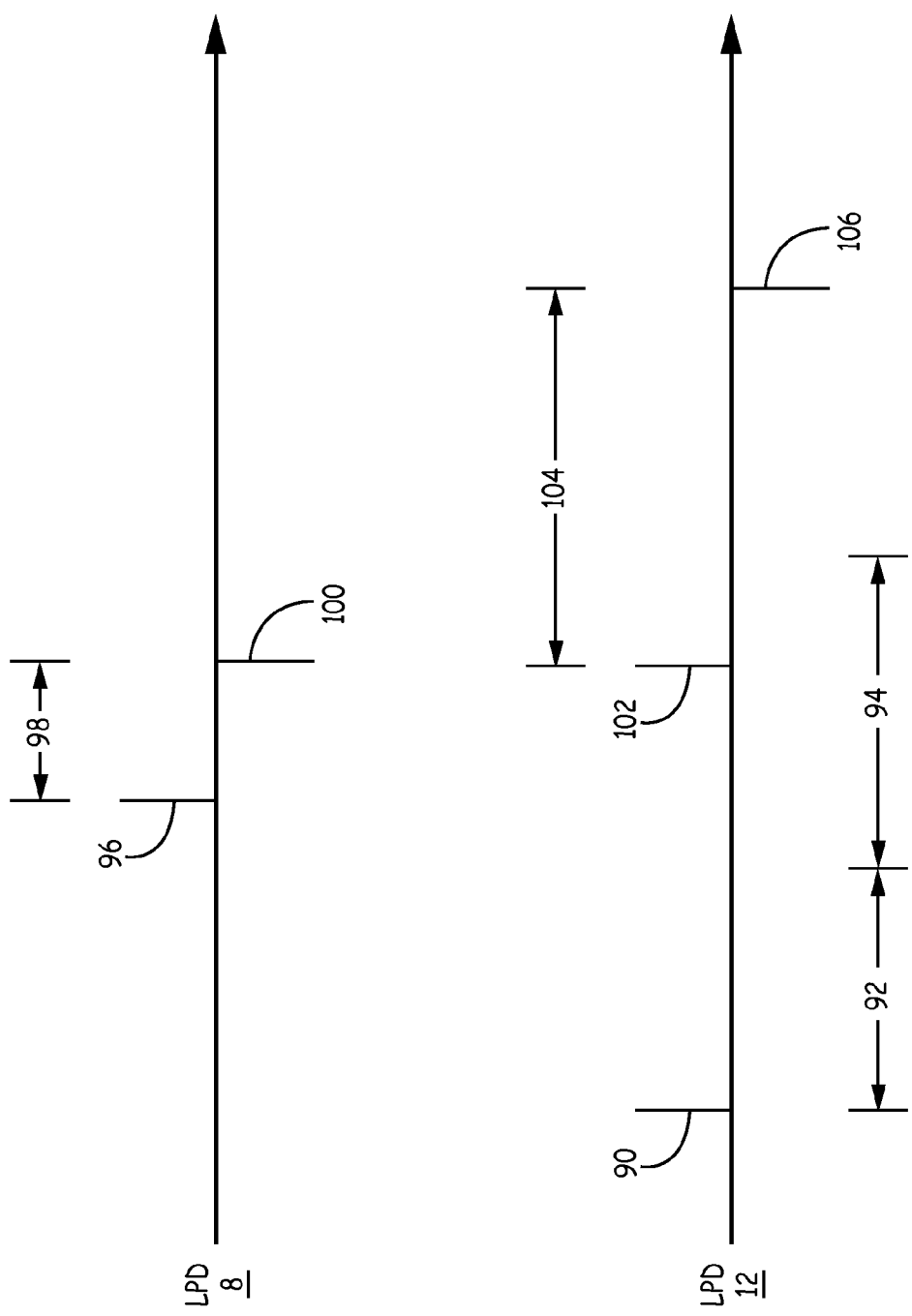
FIG. 7 is a timing diagram illustrating an example technique for coordination of ventricular pacing by a leadless pacing system.

FIG. 7 is a timing diagram illustrating an example technique for coordination of ventricular pacing by an implanted medial system, such as implanted medical system 2 that includes LPD 8 and LPD 12. As illustrated in FIG. 7, LPD 12, e.g., processing module 80 of LPD 12, may detect a ventricular depolarization 90. Processing module 80 may detect an intrinsic ventricular depolarization, e.g., R-wave, based on an indication that electrical sensing module 86 detected the depolarization via electrodes 20, 24, or may detect a paced ventricular depolarization based on an indication that signal generation module 64 delivered a pacing pulse to right ventricle 32 via electrodes 20, 24.

In response to detecting ventricular depolarization 90, processing module 80 may configure sensing module 86 to detect an electrical pulse delivered by another IMD, e.g., LPD 8, during a pulse detection window 94 that begins a predetermined pulse detection delay interval 92 after detection of detecting ventricular depolarization 90. Both pulse detection delay interval 92 and pulse detection window 94 may have predetermined lengths or durations. For example, the predetermined duration of pulse detection delay interval 92 may be approximately 400 milliseconds, and the predetermined duration of pulse detection window 94 may be 800 milliseconds or can be determined from the programmed lower pacing rate (LPR) of the LPD, e.g., as being equal to 60000/LPR—pulse detection delay interval 92.

During pulse detection window 94, electrical sensing module 86 is configured by processing module 80 to detect electrical pulses delivered by another IMD, e.g., LPD 8. For example, processing module 80 may adjust a sensitivity of electrical sensing module 86 for detection of electrical pulses delivered by another IMD during pulse detection window 94. By configuring electrical sensing module 86 to detect electrical pulses delivered by another IMD only during a pulse detection window 94 that begins a pulse detection delay interval 92 after detection of a ventricular depolarization, LPD 12 may reduce the current drain consumed by electrical sensing module 86 relative to configuring electrical sensing module 86 to detect electrical pulses delivered by another IMD at any time.

As illustrated by FIG. 7, LPD 8, e.g., electrical sensing module 66 of LPD 8, detects an intrinsic atrial depolarization 96. In response to the detection of intrinsic atrial depolarization 96, processing module 60 of LPD 8 controls signal generation module 64 to deliver an electrical pulse 100, e.g., a pacing pulse within the atrial refractory period. In some examples, processing module 60 controls signal generation module 64 to deliver electrical pulse 100 a predetermined interval 98 after detection of intrinsic atrial depolarization 96. In other examples, processing module 60 controls signal generation module 64 to deliver electrical pulse 100 closer in time to the detection of intrinsic atrial depolarization 96, e.g., immediately after the detection of intrinsic atrial depolarization 96.

A illustrated by FIG. 7, LPD 12, e.g., electrical sensing module 86 of LPD 12, detects electrical pulse 100 delivered by LPD 8 via electrodes 20, 24 at electrical pulse detection 102. In response to electrical pulse detection 102, processing module 80 of LPD 12 controls signal generation module 64 to deliver pacing pulse 106 to right ventricle 32 via electrodes 20, 24. Processing module 80 may control signal generation module 64 to deliver pacing pulse 106 a predetermined delay interval 104 after detection of electrical pulse 102.

Depending on whether LPD 8 and LPD 12 implement one or both of delay interval 98 and delay interval 104, delay intervals 98 and 104 may individually or collectively provide a desired delay between intrinsic depolarization of the other chamber and delivery of the pacing pulse to the ventricle. For example, where the other chamber is an atrium, delay intervals 98 and 104 may individually or collectively provide a desired AV delay interval. As another example, where the other chamber is a ventricle, delay intervals 98 and 104 may individually or collectively provide a desired VV delay interval.

In some examples, one or both of LPD 8 and LPD 12 may be configured to provide rate-responsive pacing by adjusting delay interval 98 or delay interval 104, respectively. To provide rate-responsive pacing, processing module 60 and/or processing module 80 may be configured to adjust delay interval 98 and/or delay interval 104, respectively, based on the output of sensor 70 and/or a determination of the current atrial rate. For example, sensor 70 may be an accelerometer that provides an indication of patient activity level, and thus demand. The processing modules may determine the current atrial rate based on a one or more previous A-A intervals, e.g., a mean or median of a number of previous A-A intervals.

Figure 8:
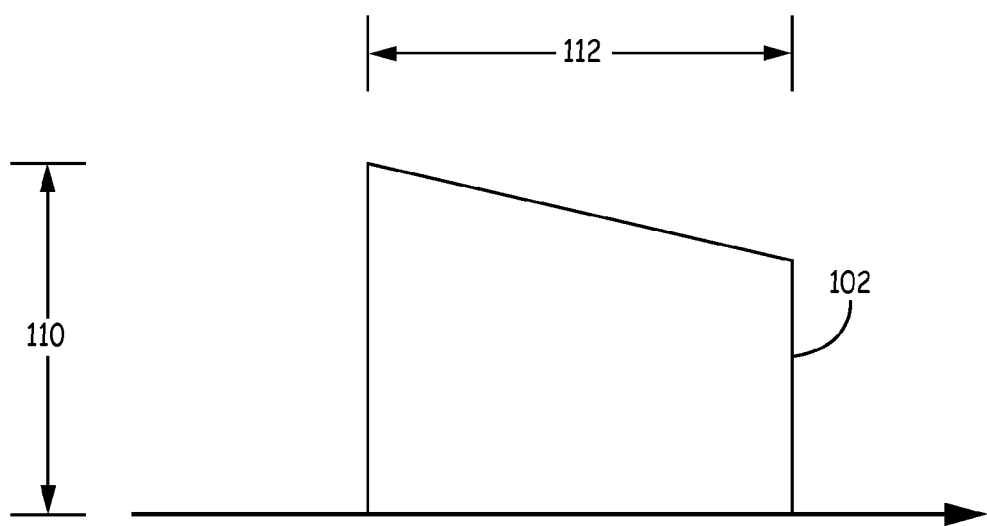
FIG. 8 is a conceptual illustration of an electrical pulse that may be generated by another implantable medical device and detected by a leadless pacing system.

FIG. 8 is a conceptual illustration of pulse 102 that may be detected by a leadless pacing system, such as leadless pacing system 10 that includes LPD 12 and sensing extension 14. As described herein, electrical sensing module 86 of LPD 12 may be configured to detect pulse 102 via electrodes 20, 24. In some examples, the other IMD, e.g., LPD 8 may be configured to deliver pulse 100 such that pulse 102 as detected by LPD 12 may have certain features that allow LPD 12, e.g., electrical sensing module 86 and/or processing module 80, to recognize pulse 102 as a pulse delivered by another IMD to indicate an intrinsic depolarization of another chamber. For example, LPD 8 may configure pulse 100 such that pulse 102 detected by LPD 12 has a predetermined amplitude 110 and/or a predetermined duration, e.g., pulse width, 112, which will cause LPD 12 to recognize pulse 112 as being delivered by another IMD to indicate intrinsic depolarization of another chamber of the heart. In some examples, LPD 8 may automatically, or as programmed by a user via programmer 40, vary pulse width 112 of pulse 102 to identify a pulse width at which LPD 12 detects pulse 102.

Figure 9:
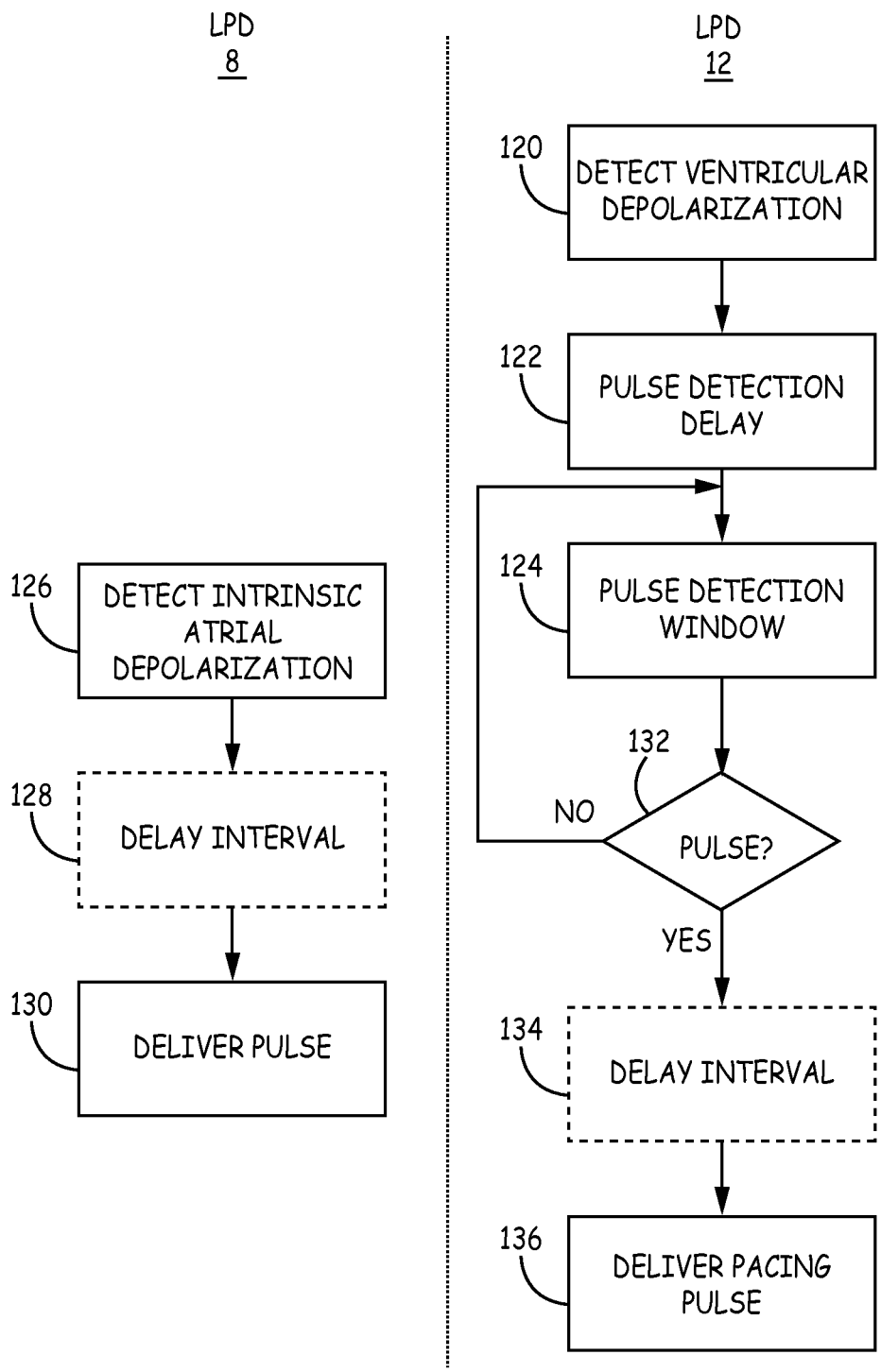
FIG. 9 is a flow diagram of an example technique for coordination of ventricular pacing by an implanted medical system.

FIG. 9 is a flow diagram of an example technique for coordination of ventricular pacing by an implanted medical system, such as implanted medical system 2 including LPD 8 and LPD 12. Although described with respect to implanted medical system 2, the example technique of FIG. 9 may be implemented in any implanted medical system, such as implanted medical systems configured to provide atrio-synchronous ventricular pacing in which LPD 8 is replaced by any IMD capable of sensing intrinsic atrial depolarizations and delivering electrical pulses, and implanted medical systems including two ventricular devices that provide CRT.

According to the example of FIG. 9, LPD 12, e.g., processing module 80, detects an intrinsic or paced ventricular depolarization 90 (120). Processing module 80 then waits a pulse detection delay interval 92 (122), and configures electrical sensing module 86 to detect electrical pulses delivered by another IMD within a pulse detection window 94 (124). Pulse detection delay interval 92 may, for example, extend approximately 400 milliseconds after detection of ventricular depolarization 90.

LPD 8, e.g., electrical sensing module 66, detects an intrinsic atrial depolarization 96 (126). In response to detecting the intrinsic atrial depolarization, LPD 8, e.g., processing module 60, controls signal generation module 64 to deliver an electrical pulse 100 (130). In some examples, processing module 60 controls the delivery of the electrical pulse a delay interval 98, e.g., AV delay interval, after the detection of the intrinsic atrial depolarization (128). In some examples, electrical pulse 100 is a pacing pulse delivered during a refractory period of the atrium.

During pulse detection window 94, LPD 12, e.g. processing module 80 of LPD 12, determines whether an electrical pulse 102 has been detected (132). When processing module 80 determines that an electrical pulse 102 has been detected (YES of 132), processing module 80 controls pulse generation module 64 to deliver a ventricular pacing pulse 106 (136). In some examples, processing module 80 controls the delivery of pacing pulse 106 a delay interval 104, e.g., an AV delay interval, after detection of the electrical pulse 102 (134).

The techniques described in this disclosure, including those attributed to LPD 8, LPD 12, programmer 40, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. An implantable medical system configured to coordinate ventricular pacing with intrinsic depolarizations of another chamber of a heart of a patient, the system comprising:
a leadless pacing system comprising:
a leadless pacing device comprising:
a stimulation module configured to generate pacing pulses;
a sensing module;
a processing module;
a housing configured to be implanted on or within a ventricle of the heart, wherein the housing encloses the stimulation module, the sensing module, and the processing module; and
a first electrode electrically coupled to the sensing module and the stimulation module; and
a sensing extension extending from the housing and comprising:
a body extending from the housing; and
a second electrode carried by the body and electrically connected to the sensing module and the stimulation module,
wherein the sensing module is configured to sense electrical activity of the ventricle via the first and second electrodes, and the stimulation module is configured to deliver pacing pulses to the ventricle via at least the first electrode; and
another implantable medical device configured to:
sense an intrinsic depolarization of the other chamber of the heart of the patient, and
in response to the intrinsic depolarization of the other chamber, deliver an electrical pulse,
wherein the sensing module of the leadless pacing device is configured to detect the electrical pulse delivered by the other implantable medical device via the first electrode and the second electrode,
wherein, in response to the sensing module of the leadless pacing device detecting the electrical pulse delivered by the other implantable medical device, the processing module of the leadless pacing device is configured to control the stimulation module of the leadless pacing device to generate a pacing pulse for delivery to the ventricle via at least the first electrode in coordination with the intrinsic depolarization of the other chamber.

2. The implantable medical system of claim 1, wherein the processing module is configured to control the stimulation module of the leadless pacing device to generate the pacing pulse for delivery to the ventricle a delay interval after the sensing module of the leadless pacing device detects the electrical pulse delivered by the other implantable medical device.

3. The implantable medical system of claim 2, wherein the other chamber is an atrium, and the delay interval is an atrio-ventricular (AV) delay interval.

4. The implantable medical system of claim 3, wherein the leadless pacing device comprises a first leadless pacing device, the stimulation module comprises a first stimulation module, the sensing module comprises a first sensing module, the processing module comprises a first processing module, and the housing comprises a first housing, and wherein the other implantable medical device comprises a second leadless pacing device comprising:
a second stimulation module configured to generate pacing pulses;
a second sensing module;
a second processing module;
a second housing configured to be implanted within the atrium, wherein the second housing encloses the second stimulation module, the second sensing module, and the second processing module, and wherein the second housing comprises a third electrode and a fourth electrode, and
wherein the second sensing module is configured to detect the intrinsic depolarization of the atrium via the third electrode and the fourth electrode,
wherein, in response to the second sensing module detecting the intrinsic depolarization of the atrium, the second processing module is configured to control the second stimulation module to deliver the electrical pulse via the third electrode and the fourth electrode, and
wherein the electrical pulse comprises a pacing pulse delivered during a refractory period of the atrium.

5. The implantable medical system of claim 2, wherein the ventricle is a first ventricle, the other chamber is a second ventricle, and the interval comprises a ventricular-ventricular (VV) delay interval.

6. The implantable medical system of claim 1, wherein the other implantable medical device is configured to deliver the electrical pulse an interval after sensing the intrinsic depolarization of other chamber of the heart.

7. The implantable medical system of claim 1, wherein the processing module of the leadless pacing device is configured to:
detect activation of the ventricle, and
configure the sensing module to detect the electrical pulse during a pulse detection window that begins a predetermined pulse detection delay interval after activation of the ventricle.

8. The implantable medical system of claim 7, wherein the processing module is configured to adjust a sensitivity of the sensing module for detection of the electrical pulse during the pulse detection window.

9. The implantable medical system of claim 1, wherein the other implantable medical device is configured to deliver the electrical pulse having a predetermined duration to indicate the depolarization of the other chamber to the leadless pacing device, and the processing module of the leadless pacing device is configured to control the stimulation module of the leadless pacing device to generate the pacing pulse for delivery to the ventricle in response to detecting the electrical pulse having the predetermined duration.

10. The implantable medical system of claim 1, wherein the body of the sensing extension is self-supporting and, when the leadless pacemaker device is implanted proximate an apex of a right ventricle of the heart, configured to extend towards a right atrium of the heart while remaining in the right ventricle of the heart.

11. The system of claim 10, wherein the self-supporting body is devoid of any fixation elements.

12. An implantable medical system configured to provide atrio-synchronous ventricular pacing, the system comprising:
a leadless pacing system comprising:
a first leadless pacing device comprising:
a first stimulation module configured to generate pacing pulses;
a first sensing module;
a first processing module;
a first housing configured to be implanted within a right ventricle of a heart of a patient, wherein the first housing encloses the first stimulation module, the first sensing module, and the first processing module; and
a first electrode electrically coupled to the first sensing module and the first stimulation module; and
a sensing extension extending from the first housing and comprising:
a body extending from the first housing; and
a second electrode carried by the body and electrically connected to the first sensing module and the first stimulation module,
wherein the first sensing module is configured to sense electrical activity of the right ventricle via the first and second electrodes, and the first stimulation module is configured to deliver pacing pulses to the right ventricle via at least the first electrode; and
a second leadless pacing device comprising:
a second stimulation module configured to generate pacing pulses;
a second sensing module;
a second processing module;
a second housing configured to be implanted within a right atrium of the heart of the patient, wherein the second housing encloses the second stimulation module, the second sensing module, and the second processing module, and wherein the second housing comprises a third electrode and a fourth electrode, and
wherein the second sensing module of the second leadless pacing device is configured to detect an intrinsic depolarization of the atrium via the third electrode and the fourth electrode,
wherein the second stimulation module of the second leadless pacing device is configured to generate pacing pulses, and
wherein, in response to the second sensing module detecting the intrinsic depolarization of the atrium, the second processing module of the second leadless pacing device is configured to control the second stimulation module of the second leadless pacing device to deliver a pacing pulse via the third electrode and the fourth electrode during a refractory period of the right atrium following the intrinsic depolarization of the right atrium,
wherein the first sensing module of the first leadless pacing device is configured to detect, via the first electrode and the second electrode, the pacing pulse delivered by the second leadless pacing device, and
wherein, in response to the first sensing module of the first leadless pacing device detecting the pacing pulse delivered by the second leadless pacing device, the first processing module of the first leadless pacing device is configured to control the first stimulation module of the first leadless pacing device to generate a pacing pulse for delivery to the right ventricle via at least the first electrode an atrio-ventricular (AV) delay interval after the first sensing module detected the pacing pulse delivered by the second leadless pacing device.

13. A method for coordinating ventricular pacing by a leadless pacing system with intrinsic depolarizations of another chamber of a heart of a patient, wherein the leadless pacing system comprises:
a leadless pacing device comprising:
a stimulation module configured to generate pacing pulses;
a sensing module;
a processing module;
a housing configured to be implanted on or within a ventricle of the heart, wherein the housing encloses the stimulation module, the sensing module, and the processing module; and
a first electrode electrically coupled to the sensing module and the stimulation module; and
a sensing extension extending from the housing and comprising:
a body extending from the housing; and
a second electrode carried by the body and electrically connected to the sensing module and the stimulation module,
wherein the sensing module is configured to sense electrical activity of the ventricle via the first and second electrodes, and the stimulation module is configured to deliver pacing pulses to the ventricle via at least the first electrode,
wherein the method comprises:
sensing, by another implantable medical device, an intrinsic depolarization of the other chamber of the heart of the patient;
in response to sensing the intrinsic depolarization of the other chamber, delivering, by the other implantable medical device, an electrical pulse;
detecting, by the sensing module of the leadless pacing device, the electrical pulse delivered by the other implantable medical device via the first electrode and the second electrode; and
in response detecting the electrical pulse delivered by the other implantable medical device, delivering, by the stimulation module of the leadless pacing device, a pacing pulse to the ventricle via at least the first electrode in coordination with the intrinsic depolarization of the other chamber.

14. The method of claim 13, wherein generating the pacing pulse for delivery to the ventricle comprises generating the pacing pulse for delivery to the ventricle a delay interval after detecting the electrical pulse delivered by the other implantable medical device.

15. The method of claim 14, wherein the other chamber is an atrium, and the delay interval is an atrio-ventricular (AV) delay interval.

16. The method of claim 15, wherein the leadless pacing device comprises a first leadless pacing device, the stimulation module comprises a first stimulation module, the sensing module comprises a first sensing module, the processing module comprises a first processing module, and the housing comprises a first housing, and wherein the other implantable medical device comprises a second leadless pacing device comprising:
a second stimulation module configured to generate pacing pulses;
a second sensing module;
a second processing module;
a second housing configured to be implanted within the atrium, wherein the second housing encloses the second stimulation module, the second sensing module, and the second processing module, and wherein the second housing comprises a third electrode and a fourth electrode, and
wherein detecting the intrinsic depolarization of the other chamber comprises detecting, by the second sensing module of the second leadless pacing device, the intrinsic depolarization of the atrium via the third electrode and the fourth electrode, and
wherein delivering the electrical pulse comprises delivering, in response to detecting the intrinsic depolarization of the atrium, by the second stimulation module of the second leadless pacing device, a pacing via the third electrode and the fourth electrode during a refractory period of the atrium.

17. The method of claim 14, wherein the ventricle is a first ventricle, the other chamber is a second ventricle, and the interval comprises a ventricular-ventricular (VV) delay interval.

18. The method of claim 13, wherein delivering the electrical pulse comprises delivering, by the other implantable medical device, the electrical pulse an interval after sensing the intrinsic depolarization of other chamber of the heart.

19. The method of claim 13, further comprising:
detecting, by the processing module of the leadless pacing device, activation of the ventricle; and
configuring, by the processing module of the leadless pacing device, the sensing module to detect the electrical pulse during a pulse detection window that begins a predetermined pulse detection delay interval after activation of the ventricle.

20. The method of claim 19, wherein configuring the sensing module to detect the electrical pulse during the pulse detection window comprises adjusting a sensitivity of the sensing module for detection of the electrical pulse during the pulse detection window.

21. The method of claim 13, wherein delivering the electrical pulse comprises delivering, by the other implantable medical device, the electrical pulse with a predetermined duration to indicate the depolarization of the other chamber to the leadless pacing device, and wherein delivering the pacing pulse comprises delivering, by the stimulation module of the leadless pacing device, the pacing pulse to the ventricle in response to detecting the electrical pulse having the predetermined duration.

* * * * *